United States Patent

Fujiwara et al.

[11] Patent Number: 6,080,172
[45] Date of Patent: Jun. 27, 2000

[54] DEVICE FOR STABBING A CORNEUM LAYER

[75] Inventors: Hidetaka Fujiwara; Toru Matsumoto, both of Tokyo, Japan

[73] Assignee: NEC Corporation, Tokyo, Japan

[21] Appl. No.: 09/087,865

[22] Filed: Jun. 1, 1998

[30] Foreign Application Priority Data

May 30, 1997 [JP] Japan ................................... 9-142111

[51] Int. Cl.⁷ ...................................................... A61F 9/00
[52] U.S. Cl. .......................................................... 606/166
[58] Field of Search .................................. 606/166, 180, 606/167, 161, 107; 623/5; 604/22

[56] References Cited

U.S. PATENT DOCUMENTS

| | | | |
|---|---|---|---|
| 4,815,463 | 3/1989 | Hanna | 606/166 |
| 4,997,437 | 3/1991 | Grieshaber | 606/166 |
| 5,290,301 | 3/1994 | Lieberman | 606/166 |
| 5,312,428 | 5/1994 | Lieberman | 606/166 |
| 5,441,511 | 8/1995 | Hanna | 606/166 |

FOREIGN PATENT DOCUMENTS

| | | |
|---|---|---|
| 52-108898 | 8/1977 | Japan . |
| 2-286132 | 11/1990 | Japan . |
| 4-341241 | 11/1992 | Japan . |
| 6-121796 | 5/1994 | Japan . |
| 7-132119 | 5/1995 | Japan . |
| 7-255706 | 10/1995 | Japan . |
| 9-51878 | 2/1997 | Japan . |
| 9-89885 | 4/1997 | Japan . |

OTHER PUBLICATIONS

M. Kikuchi et al., "Novel Method for Non–Invasive Measurement of Biomedical Substances in Blood", *12th C.M.B.E.C., 1st Pan. Pacific Symposium*, Vancouver, Canada 1986, pp. 1–2.

J. Kimura et al., "A Novel Blood Glucose Monitoring Method: An ISFET Biosensor Application to Transcutaneous Effusion Fluid", *Proceedings of the Symposium on Chemical Sensors*, vol. 87–9, pp. 327–333.

N. Ito et al., "Development of a transcutaneous blood–constituent . . . and an ion–sensitive field–effect transistor glucose sensor", *Medical & Biological Engineering & Computing*, May 1994, pp. 242–246.

Primary Examiner—Michael Buiz
Assistant Examiner—(Jackie) Tan-Uyen Tho
Attorney, Agent, or Firm—Sughrue, Mion, Zinn, Macpeak & Seas, PLLC

[57] ABSTRACT

A corneum layer stabbing device of the present invention frees a patient or subject from physical and psychological pains and realizes rapid curing. After a casing has been positioned on a skin, an electromagnet is energized to move a needle or needles mounted on a shaft until they stab the skin and penetrate a corneum layer. When the electromagnet is deenergized, the shaft returns to its original position due to the action of a spring, moving the needles away from the skin. As a result, holes are formed in the corneum layer of the skin.

16 Claims, 7 Drawing Sheets

DEVICE FOR STABBING A CORNEUM LAYER

BACKGROUND OF THE INVENTION

The present invention relates to a corneum layer stabbing device usable to measure the chemical components of an interstitial fluid produced by suction, particularly to collect a tissue fluid below the corneum of a skin.

It has been customary to measure the contents of glucose, lactate, urea nitrogen and other chemical substances existing in an organism by collecting blood. The content of each component is measured on the basis of a change in the color of a test paper, a light absorption degree, or an electric signal output from a biosensor. Such measuring methods have recently been improved to such an extent that even a sample of several microliters can be measured. To collect blood, a needle is usually penetrated into the vein of, e.g., an arm. On the other hand, when the amount of blood necessary for measurement is only several microliters, a fine needle having an inside diameter as small as several microns may be penetrated into a capillary. However, it is difficult to accurately position and insert such a fine needle into a capillary. In light of this, a method using a blood collecting device having a number of fine hollow needles has been proposed in, e.g., Japanese Patent Laid-Open Publication No. 7-132119. This method makes it needless to position a single needle.

On the other hand, measuring methods using an interstitial fluid collected from a skin in place of blood have been proposed and disclosed in, e.g., Proc. of the First Pan Pacific Symposium, Vancouver, Canada, Jul. 23–27, 1986, pp. 57–58 and Proc. of the Symposium of the Chemical Sensors, PV87-9, pp.327–333.

An interstitial fluid is a trace of liquid produced by removing a corneum layer from a part the skin of, e.g., an arm and then depressurizing the same part. The interstitial fluid is generally considered to be a fluid existing in a hypodermic tissue or a liquid filtered via a capillary wall due to depressurization. Because the interstitial fluid produced by suction is lower in a protein content than blood, it reduces the deposition of proteins on the surface of a sensor during measurement and thereby extends the life of the sensor. In addition, collecting an interstitial fluid via a skin reduces the subject's pain and contagion, compared to the collection of blood. This kind of method is taught in, e.g., Japanese Patent Laid-Open Publication No. 4-341241 by way of example.

The conventional blood collecting device has a problem that needles are formed by a silicon nitride film as thin as 1 $\mu m$ and therefore extremely fragile and cannot easily penetrate a skin. Another problem is that the needles penetrated a skin are apt to bend and stop holes or to be left in the subject's body. Moreover, when blood is passed through a fine tube whose diameter is as small as several tens of microns, red blood cells present in the blood and having a diameter of about 10 $\mu m$ to 20 $\mu m$ are destroyed (hemolysis). This changes the contents of chemical substances existing in the blood.

The conventional method of measuring an interstitial fluid produced by suction solves the above problems, but brings about other problems, as follows. A first problem is that a tape stripping method used to remove the corneum layer needs expertness. Specifically, the thickness of a corneum layer and how it comes off depend on the portion, age and sex. Should the removal of a corneum layer be insufficient, an interstitial fluid would not be collected. Should the removal be excessive, it would cause bleeding and pain to occur. Therefore, to remove a corneum layer to a depth great enough to collect an interstitial fluid without any bleeding, careful operation relying on experience and perception is necessary.

A second problem is that the removal of a corneum layer is a burden on a subject or patient both physically and psychologically because the patient is required to stay still for more than 30 minutes until the end of the removal.

A third problem is that a skin does not cure rapidly.

That is, a skin from which a corneum layer has been removed does not regenerate for about two weeks.

A fourth problem is that it is difficult to remove a corneum layer evenly, resulting in inefficient interstitial fluid collection. Specifically, the amount of collection of an interstitial fluid is proportional to the area of removal of a corneum layer. In a corneum layer, basement cells below corneum repeat division with the result that keratinocytes are stacked on a skin in the form of scales. The tape stripping method renders the removal of such a corneum layer irregular and cannot remove a desired area evenly.

Technologies relating to the present invention are also disclosed in, e.g., Medical and Biological Engineering & Computing, May 1994, pp. 242–246 and Japanese Patent Laid-Open Publication Nos. 2-286132 and 6-121796.

SUMMARY OF THE INVENTION

It is therefore an object of the present invention to provide a corneum layer stabbing device for suction type interstitial fluid collection and capable of pretreating a skin by a simple procedure while freeing a patient from physical and psychological pains and promoting the rapid cure of the skin.

A device for stabbing a corneum layer of the present invention includes a support supporting a shaft such that the shaft is movable in the up-and-down direction. A needle holder is mounted on the bottom of the shaft and holds at least one needle for forming a hole in the corneum layer. The needle protrudes downward from the underside of the needle holder. A moving member causes the shaft to move in the up-and-down direction.

Also, a device for stabbing a corneum layer of the present invention includes a needle holder roller having needles thereon, and an arrangement for causing the needle holder roller to rotate.

BRIEF DESCRIPTION OF THE DRAWINGS

The above and other objects, features and advantages of the present invention will become apparent from the following detailed description taken with the accompanying drawings in which.

DESCRIPTION OF THE PREFERRED EMBODIMENTS

Figure 1:
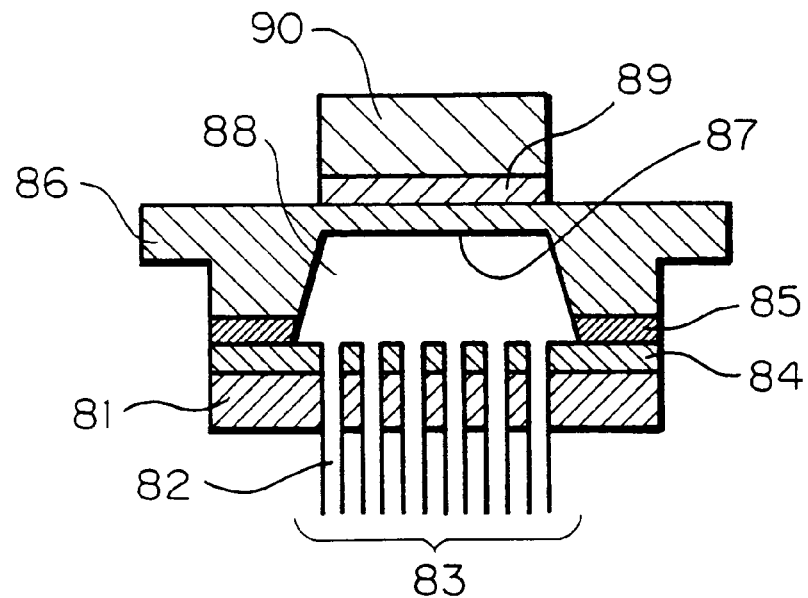
FIG. 1 is a sectional front view showing a conventional blood collecting device.

To better understand the present invention, brief reference will be made to a conventional blood collecting device, shown in FIG. 1. As shown, the device includes a first silicon substrate 81 formed with a number of through openings 82 each having a diameter of 10 μm to 50 μm. An about 1 μm thick silicon nitride film 84 is formed on the rear of the substrate 81 and the walls of the openings 82 contiguous therewith. The film 84 on the walls of the openings 82 is extended to the outside over the front of the silicon substrate 81, forming a number of hollow needles 83. A second silicon substrate 86 is adhered to the rear of the substrate 81 with the intermediary of an adhesion layer 85. The center portion of the second silicon substrate 86 is implemented as a thin membrane 87. A bore 88 is formed at the rear of the needles 83. An Au (gold) film 89 is formed on the rear of the membrane 87 while a microheater 90 is provided on the rear of the Au film 89, i.e., on the top of the assembly, as viewed in FIG. 1. To collect blood, the needles 83 are pushed into a skin, and then the microheater 90 is caused to heat. As a result, the membrane 87 expands due to a difference between the coefficient of thermal expansion o f Au and that of silicon such that the bore 88 expands. In this condition, blood is collected due to vacuum generated in the bore 88 and needles 83.

The above blood collecting device has a problem that the needles 83 implemented by the silicon nitride film 84 as thin as 1 μm are extremely fragile and cannot easily penetrate a skin. Another problem is that the needles 83 penetrated a skin are apt to bend and stop holes or to be left in the subject's body. Moreover, when blood is passed through a fine tube whose diameter is as small as several tens of microns, red blood cells present in the blood and having a diameter of about 10 μm to 20 μm are destroyed (hemolysis). This changes the contents of chemical substances existing in blood.

Figure 2:
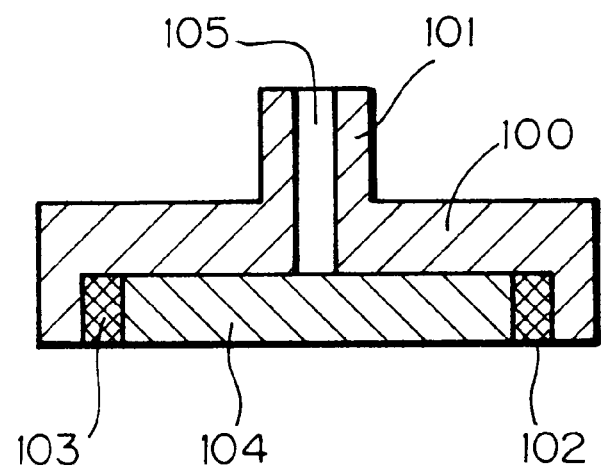
FIG. 2 is a section showing a suction type conventional interstitial fluid collecting device.

FIG. 2 shows a conventional suction type interstitial fluid collecting device. As shown, the device includes a cell 100 having a suction port 101 at one end and an opening 102 at the other end. A mesh 104 is received in the opening 102 and fixed in place by a frame 103. To collect an interstitial fluid, a comeum layer is stripped off from the intended portion of a skin by use of a tape (tape stripping method). Then, the mesh 104 is brought into contact with the skin from which the corneum layer has been removed. Subsequently, the end of the cell 100 is caused to closely contact the skin. In this condition, the cell 100 is depressurized by, e.g., a vacuum pump via the suction port 101. As a result, an interstitial fluid effuses from the skin and is collected via a passageway 105. This kind of collecting device has the first to fourth problems stated earlier.

Figure 3:
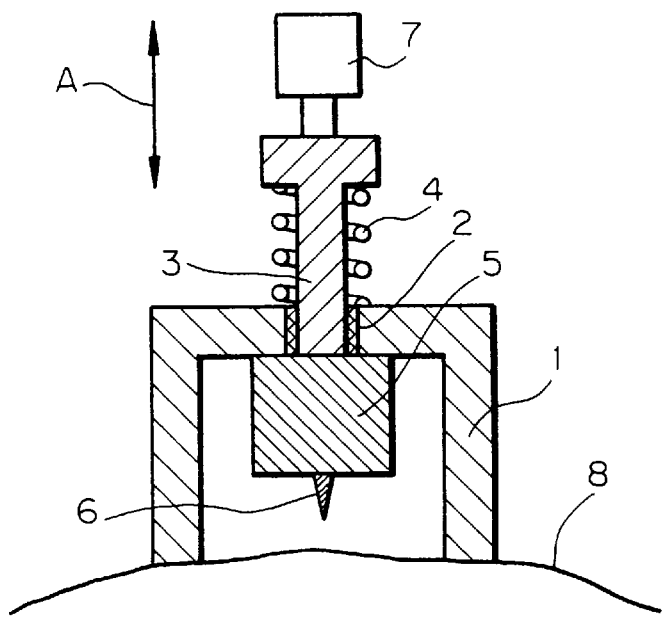
FIGS. 3–6 are sectional front views showing a first to a fourth embodiment of the present invention, respectively.

Referring to FIG. 3, a skin stabbing device embodying the present invention is shown and used to stab a corneum layer. As shown, the device includes a cylindrical casing or support 1. A bearing 2 is fitted on the top of the casing 1 in order to smoothly guide a shaft 3 linearly in a direction indicated by an arrow A. An electromagnet 7 is affixed to the top of the shaft 3. A spring 4 surrounds the shaft 3 and constantly biases the shaft 3 upward. A needle holder 5 is mounted on the bottom of the shaft 3 and held at a preselected distance from the lower end of the casing 1. A needle 6 protrudes from the needle holder 5 downward in order to penetrate the corneum layer of a skin 8.

In operation, after the casing 1 has been positioned on the skin 8, the electromagnet 7 is energized. In response, the shaft 3 is moved toward the skin 8 until the needle 6 of the needle holder 5 stabs the skin 8 and penetrates the corneum layer thereof. Subsequently, when the electromagnet 7 is deenergized, the shaft 3 returns to its initial position due to the action of the spring 4, moving the needle 6 away from the skin 8. As a result, a hole is formed in the corneum layer of the skin 8. This action completes instantaneously and causes the patient or subject to feel hardly any pain because the needle is less than 500 μm long. After the above procedure, a suction type interstitial fluid collecting device, not shown, is positioned on the skin 8 and then depressurized. Consequently, the skin 8 is deformed and enlarges the hole, causing an interstitial fluid to effuse.

Figure 4:
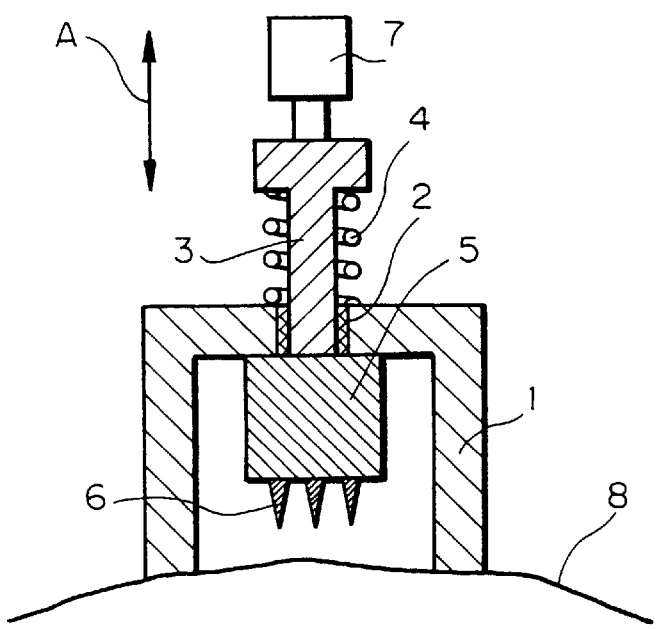

FIG. 4 shows a second embodiment of the present invention which is a modification of the first embodiment. As shown, the needle holder 5 holds a plurality of needles 6 for forming a plurality of holes in the skin 8 at a time. As for the rest of the construction, this embodiment is identical with the first embodiment. This embodiment has an advantage that because the amount of an interstitial fluid to be collected is proportional to the number of holes, a greater amount of interstitial fluid can be collected in a shorter period of time.

Figure 5:
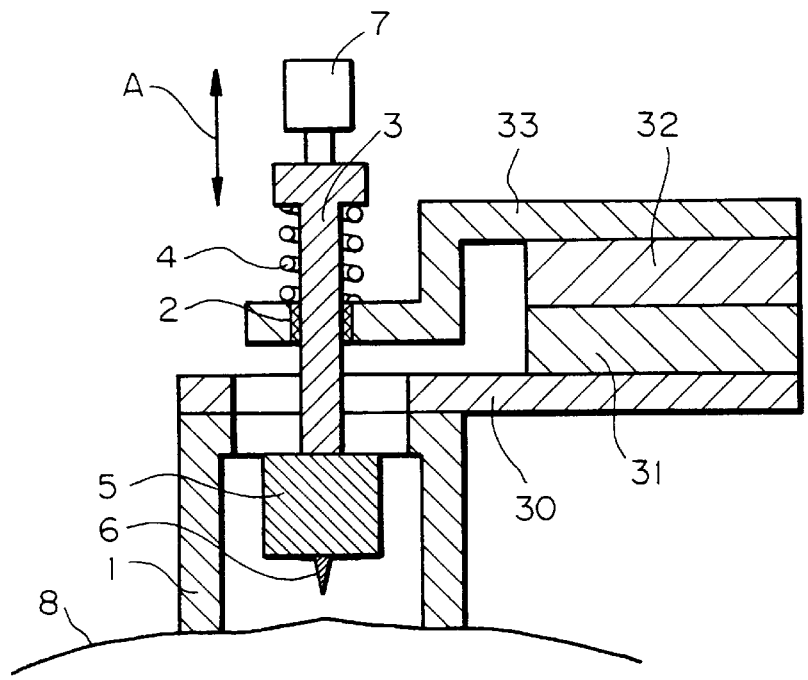

FIG. 5 shows a third embodiment of the present invention which is another modification of the first embodiment. As shown, a base 30 is mounted on the top of the casing 1. A first stage 31, a second stage 32 and a shaft support plate 33 are mounted on the top of the base 30. The first and second stages 31 and 32 are movable horizontally and movable perpendicularly to each other. The shaft support plate 33 supports the shaft 3. In the illustrative embodiment, the bearing 2 is fitted on the shaft support plate 3 in order to smoothly guide the shaft 3 in the up-and-down direction. In operation, after the casing 1 has been positioned on the skin 8, the stages 31 and 32 are moved to bring the shaft support plate 33 to a desired position. Then, the needle 6 is caused to stab the skin 8 in exactly the same manner as in the first embodiment. Such a procedure may be repeated in order to form a plurality of holes in the skin 8.

Figure 6:
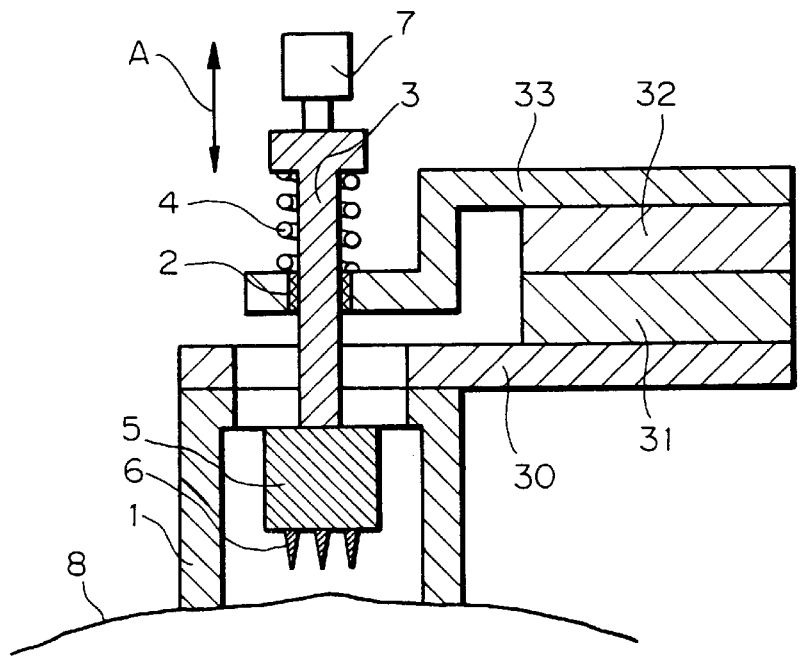

FIG. 6 shows a fourth embodiment of the present invention which is a modification of the third embodiment. As shown, this embodiment is identical with the third embodiment except that the needle holder 5 holds a plurality of needles 6. This embodiment has the same advantage as the second embodiment.

Figure 7A:
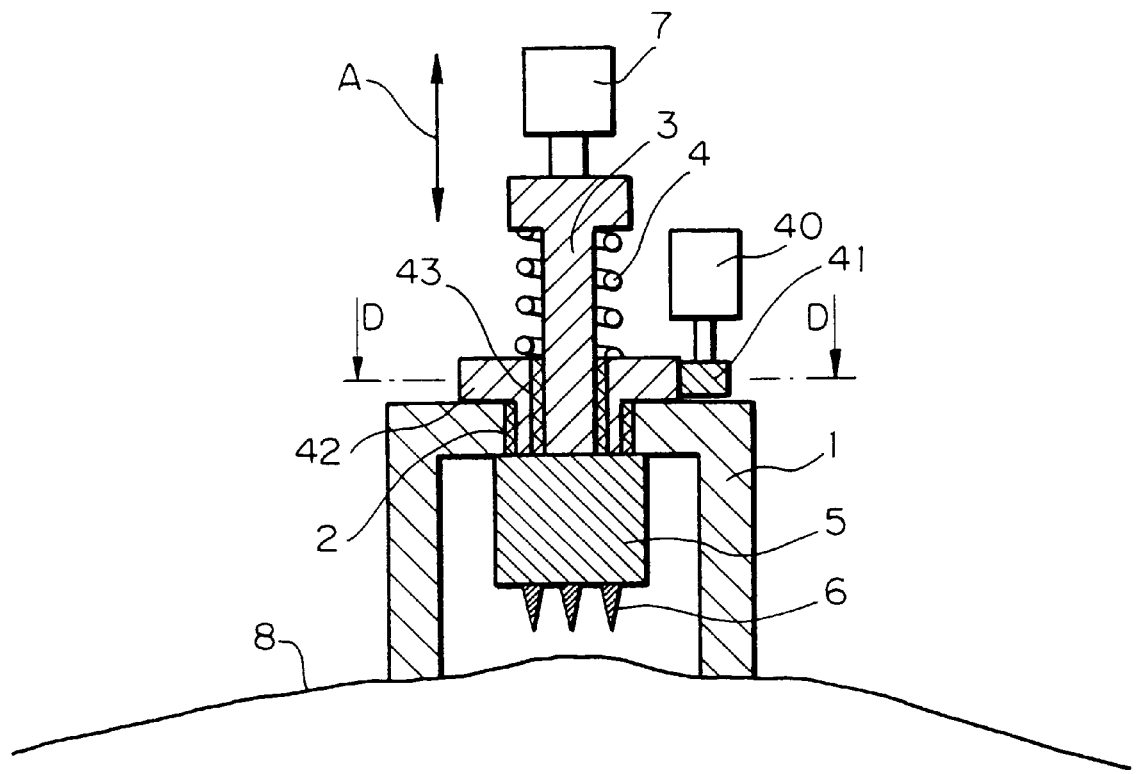
FIG. 7A is a sectional front view showing a fifth embodiment of the present invention.
Figure 7B:
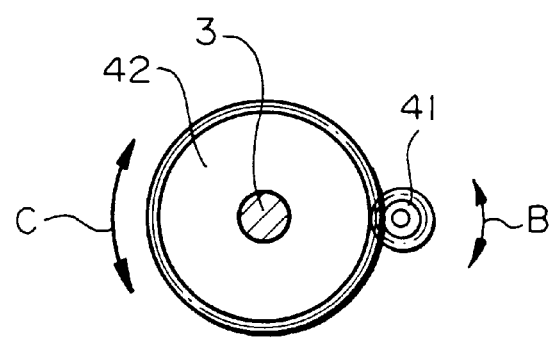
FIG. 7B is a sectional top view as seen in a direction D—D of FIG. 7A.

Reference will be made to FIGS. 7A and 7B for describing a fifth embodiment of the present invention which is a modification of the second embodiment. As shown, a first gear 41 is mounted on the output shaft of a motor or drive source 40. A second gear 42 is mounted on the top of the casing 1 with the intermediary of a rotary bearing 43. The gear 42 is held in mesh with the gear 41 so as to be rotated by the motor 40. The shaft 3 is mounted on the center of the gear 42 with the intermediary of the bearing 3 and movable up and down smoothly. The needle holder 5 holding a plurality of needles 6 is affixed to the bottom of the shaft 3.

In operation, after the casing 1 has been positioned on the skin 8, the electromagnet 7 is energized. In response, the shaft 3 is moved toward the skin 8 until the needles 6 of the needle holder 5 stab the skin 8 and penetrate the corneum layer thereof. Subsequently, when the electromagnet 7 is deenergized, the shaft 3 returns to its initial position due to the action of the spring 4, moving the needles 6 away from the skin 8. As a result, holes are formed in the corneum layer of the skin 8. Thereafter, the motor 40 is rotated by a desired angle in a direction indicated by an arrow B. The motor 40 rotates the second gear 42 via the first gear 41 in a direction indicated by an arrow C. Consequently, the shaft 3 is rotated to bring the needles 6 to positions different from the previous positions where they formed the holes in the skin 8. Such a procedure may be repeated in order to form a plurality of holes.

Figure 8A:
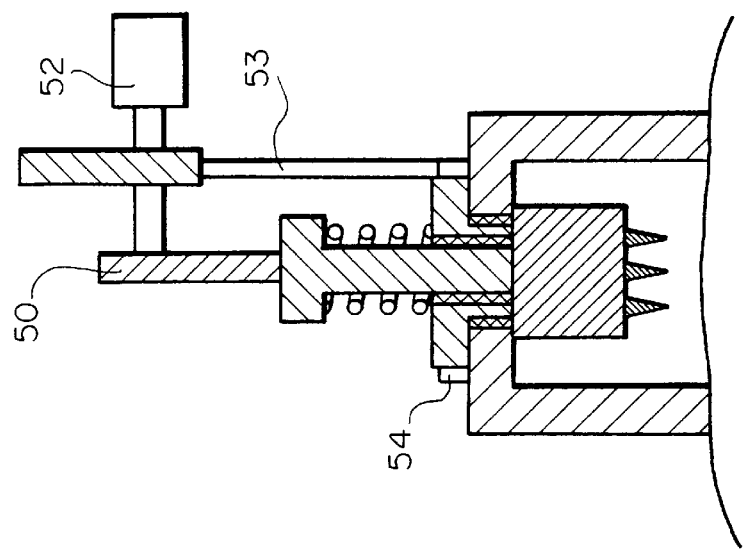
FIG. 8A is a sectional front view showing a sixth embodiment of the present invention.
Figure 8B:
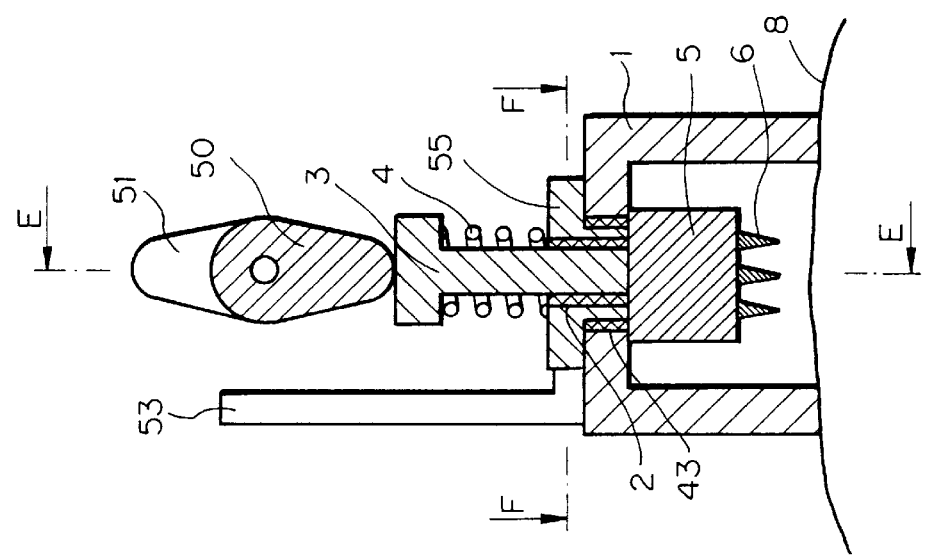
FIG. 8B is a sectional side elevation as seen in a direction E—E of FIG. 8A.
Figure 8C:
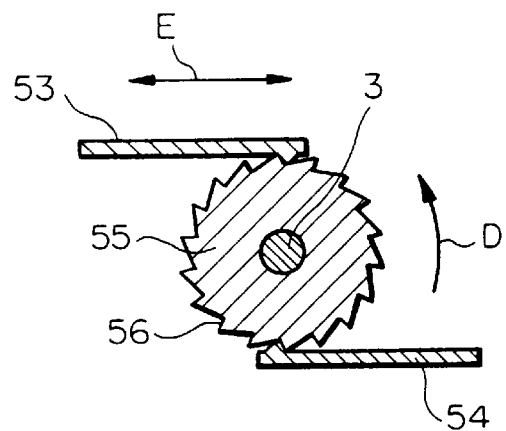
FIG. 8C is a sectional top view as seen in a direction F—F of FIG. 8A.

FIGS. 8A–8C show a sixth embodiment of the present invention which is a modification of the fifth embodiment. As shown, a rotatable shaft 55 is mounted on the top of the casing 1 with the intermediary of the rotary bearing 43. A ratchet 56 in the form of saw-teeth is formed in the circumferential surface of the rotary shaft 55. A fixing pawl 54 is engaged with the ratchet 56 in order to allow the rotary shaft 55 to rotate in only one direction indicated by an arrow D. A first cam 50 for moving the shaft 3 up and down and a second cam 51 for angularly moving a moving pawl 53 are mounted on the output shaft of a motor 52. The moving pawl 53 is movable in a direction indicated by an arrow E in mesh with the ratchet 56.

In operation, after the casing 1 has been positioned on the skin 8, the motor 52 is driven to cause the first cam 50 to move the shaft 3 toward the skin 8 until the needles 6 of the needle holder 5 stab the corneum layer of the skin 8. When the motor 52 is deenergized, the shaft 3 returns to its original position due to the action of the spring 4, moving the needles 6 away from the skin 8. As a result, holes are formed in the corneum layer of the skin 8. Then, the second cam 51 moves the moving pawl 53 such that the rotary shaft 55 and ratchet 56 move by one pitch and bring the needles 6 to positions different from the previous positions where they formed the holes. Such a procedure may be repeated in order to form a plurality of holes.

Figure 9A:
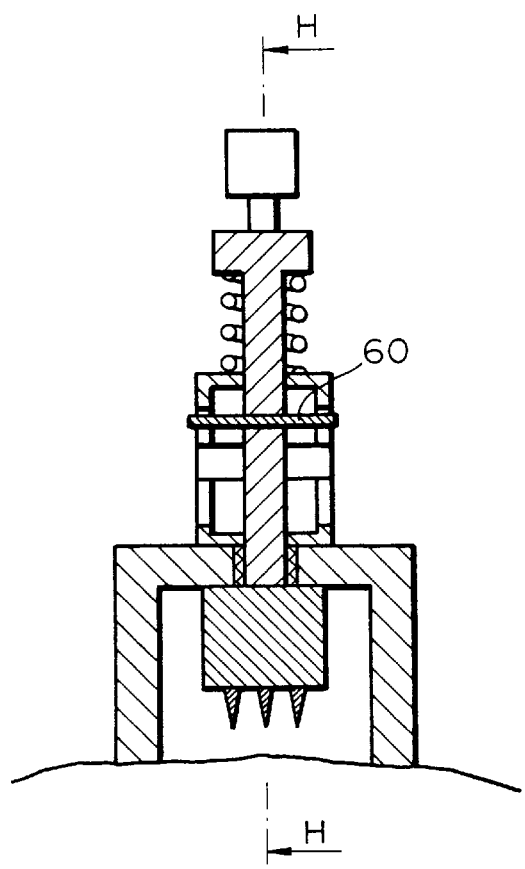
FIG. 9A is a sectional front view showing a seventh embodiment of the present invention.
Figure 9B:
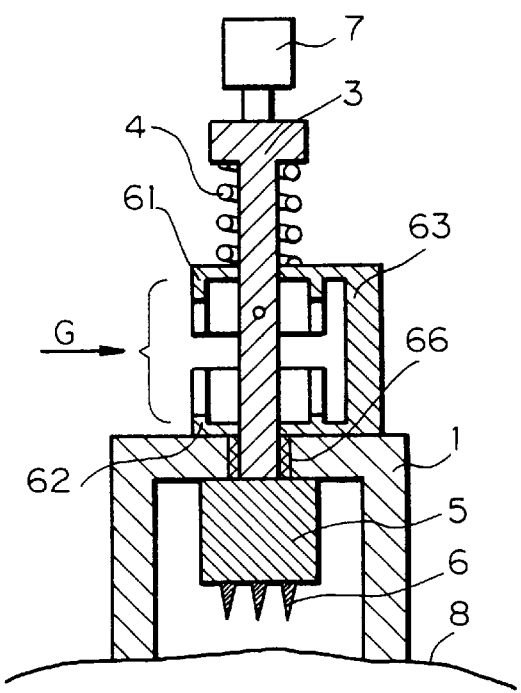
FIG. 9B is a sectional side elevation as seen in a direction H—H of FIG. 9A.
Figure 9C:
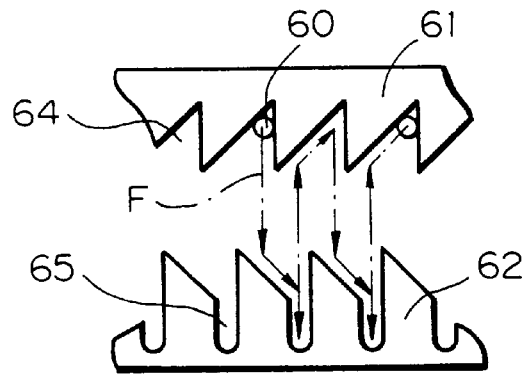
FIG. 9C is a fragmentary enlarged view of a portion G shown in FIG. 9A.

FIGS. 9A–9C show a seventh embodiment of the present invention which is a modification of the fifth embodiment. As shown, the shaft 3 is mounted on the top of the casing 1 with the intermediary of a bearing 66 such that it is capable of rotating and moving up and down smoothly. A pin 60 is mounted on the shaft 3. A guide and support portion 63 includes a first guide 61 formed with a first groove 64 and a second guide 62 formed with a second groove 65. The pin 60 is selectively rotatable along either one of the first and second grooves 64 and 65.

In operation, after the casing 1 has been positioned on the skin 8, the electromagnet 7 is energized to move the shaft 3 toward the skin 8. At this instant, the pin 60 of the shaft 3 moves along the second groove 65 of the second guide 62 in a direction indicated by an arrow F. After the shaft 3 has been rotated to a desired angular position, the needles 6 are caused to stab the corneum layer of the skin 8. When the electromagnet 7 is deenergized, the shaft 3 returns to its original position due to the action of the spring 4. At this instant, the pin 60 moves along the first groove 64 of the first guide 61 to a position where it can start moving along the second groove 65. Such a procedure may be repeated in order to form a plurality of holes in the skin 8.

Figure 10A:
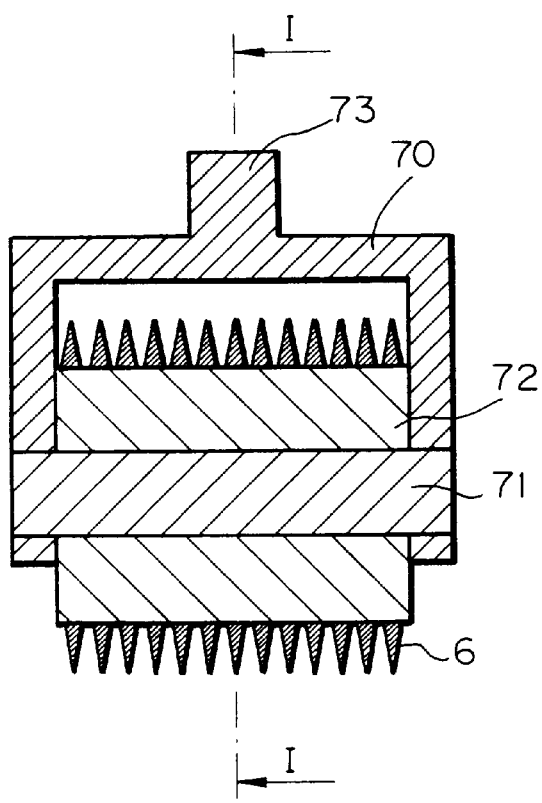
FIG. 10A is a sectional front view showing an eighth embodiment of the present invention.
Figure 10B:
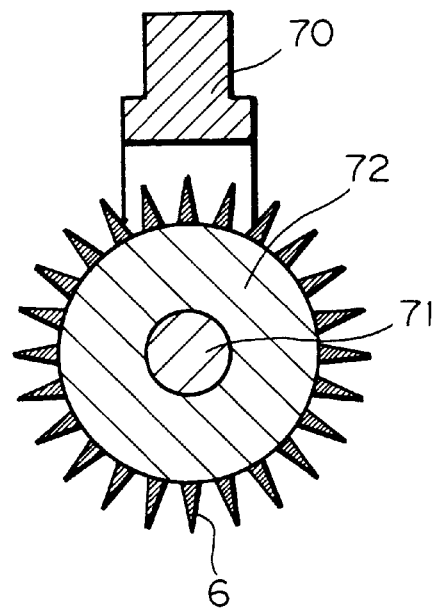
FIG. 10B is a sectional side elevation as seen in a direction I—I of FIG. 10A.

FIGS. 10A and 10B show an eighth embodiment of the present invention. As shown, a shaft 71 is mounted on a frame or support 70. A needle holder roller 72 is rotatably mounted on the shaft 71 and holds a plurality of needles 6. In operation, the needle holder roller 72 is pressed against the skin 8 with a thumb piece 73 being held by finger, so that the needles 6 stab the corneum layer of the skin 8. Subsequently, the frame 70 is moved in the parallel direction, causing the roller 72 to rotate. As a result, other needles 6 of the roller 72 stab the corneum layer. In this manner, a plurality of holes are formed in the skin 8.

In summary, it will be seen that the present invention provides a corneum layer stabbing device having various unprecedented advantages, as enumerated below.

(1) The device allows even an untrained person to easily collect an interstitial fluid via holes formed in the corneum layer of a skin. Specifically, needles protruding from the device should only be caused to penetrate the corneum layer.

(2) Because the needles are extremely fine and do not stimulate pain spots, the patient feels hardly any pain. This successfully reduces a burden on the patient both physically and psychologically.

(3) The skin cures rapidly because the holes formed in the skin each is as small as several tens of microns and closed up due to the elasticity of the skin.

Various modifications will become possible for those skilled in the art after receiving the teachings of the present disclosure without departing from the scope thereof.

What is claimed is:

1. A device for stabbing a corneum layer, comprising:
   support means supporting a shaft such that said shaft is movable in an axial up-and-down direction;
   needle holding means mounted on a bottom of said shaft and holding at least one needle for forming a hole in the corneum layer, said at least one needle protruding downward from an underside of said needle holding means; and
   moving means for moving said shaft in the axial up-and-down direction so that at least one needle for forming said hole moves rapidly in said up-and-down direction in the corneum layer.

2. A device as claimed in claim 1, further comprising an electromagnet included in said moving means for moving said shaft in at least a downward direction.

3. A device as claimed in claim 2, wherein said support means causes said shaft to move in an X and a Y axis direction.

4. A device as claimed in claim 1, wherein said support means causes said shaft to rotate about an axis thereof.

5. A device as claimed in claim 4, wherein said support means includes cam means for moving said shaft in the up-and-down direction and a moving pawl for causing said shaft to rotate.

6. A device as claimed in claim 1, wherein said support means causes said shaft to move in an X and a Y direction.

7. A device as claimed in claim 1, wherein said support means includes cam means for moving said shaft in the up-and-down direction and a moving pawl for causing said shaft to rotate.

8. A device for stabbing a corneum layer, comprising:
   support means supporting a shaft such that said shaft is movable in an up-and-down direction;
   needle holding means mounted on a bottom of said shaft and holding at least one needle for forming a hole in the corneum layer, said at least one needle protruding downward from an underside of said needle holding means; and moving means for moving said shaft in the up-and-down direction;

wherein an electromagnet is included in said moving means for moving said shaft in at least a downward direction.

9. A device as claimed in claim 8, wherein said support means causes said shaft to move in an X and a Y axis direction.

10. A device for stabbing a corneum layer, comprising:

a support supporting a shaft, said shaft being moveable in an axial up-and-down direction with respect to said support; and a needle holder mounted on a bottom of said shaft, holding at least one needle for forming a hole in the corneum layer, said at least one needle protruding from an underside of said needle holder.

11. A device as claimed in claim 10, further comprising an electromagnet mounted on said shaft for moving said shaft in at least a downward direction.

12. A device as claimed in claim 10, further comprising a biasing element surrounding said shaft and constantly biasing said shaft in at least an upward direction.

13. A device as claimed in claim 11, wherein said shaft supported by said support is movable in an X and a Y axis direction.

14. A device as claimed in claim 10, wherein said shaft supported by said support is rotatable about an axis thereof.

15. A device as claimed in claim 14, wherein said shaft further comprises at least one cam mounted thereon for moving said shaft in said up-and-down direction and a moving pawl for causing said shaft to rotate.

16. A device as claimed in claim 10, wherein said shaft further comprises at least one cam mounted thereon for moving said shaft in said up-and-down direction and a moving pawl for causing said shaft to rotate.

* * * * *